US012211211B2

United States Patent
Rabbani et al.

(10) Patent No.: US 12,211,211 B2
(45) Date of Patent: Jan. 28, 2025

(54) CORNEAL EPITHELIUM SEGMENTATION IN OPTICAL COHERENCE TOMOGRAPHY IMAGES

(71) Applicant: Alcon Inc., Fribourg (CH)

(72) Inventors: Parisa Rabbani, Aliso Viejo, CA (US); Sahar Hosseinzadeh Kassani, Lake Forest, CA (US)

(73) Assignee: Alcon Inc., Fribourg (CH)

(*) Notice: Subject to any disclaimer, the term of this patent is extended or adjusted under 35 U.S.C. 154(b) by 378 days.

(21) Appl. No.: 17/453,559

(22) Filed: Nov. 4, 2021

(65) Prior Publication Data
US 2022/0148187 A1 May 12, 2022

Related U.S. Application Data

(60) Provisional application No. 63/112,833, filed on Nov. 12, 2020.

(51) Int. Cl.
  *G06T 7/11* (2017.01)
  *A61B 3/10* (2006.01)
  (Continued)

(52) U.S. Cl.
  CPC .............. *G06T 7/11* (2017.01); *A61B 3/102* (2013.01); *A61B 3/107* (2013.01); *G06T 7/136* (2017.01);
  (Continued)

(58) Field of Classification Search
  CPC . G06T 7/11; G06T 7/194; G06T 7/136; G06T 7/149; G06T 7/70;
  (Continued)

(56) References Cited

U.S. PATENT DOCUMENTS 9,655,512 B2 * 5/2017 Huang ................. A61B 3/1005
10,468,142 B1 * 11/2019 Abou Shousha ...... G16H 30/20
(Continued)

OTHER PUBLICATIONS

Dos Santos et al., "CorneaNet: fast segmentation of cornea OCT scans of healthy and keratoconic eyes using deep learning," Biomedical optics express, vol. 10,2 622-641, Jan. 17, 2019, doi:10. 1364/BOE.10.000622 (Year: 2019).*
(Continued)

*Primary Examiner* — Ming Y Hon
*Assistant Examiner* — Julia Z. Yao
(74) *Attorney, Agent, or Firm* — Patterson + Sheridan, LLP

(57) ABSTRACT

The techniques described herein provide improved techniques for segmenting corneal epithelium layer. A method includes receiving an optical coherence tomography (OCT) image of an eye; generating, based on the OCT image, a binarized image of the eye; generating, based on the binarized image of the eye and the OCT image, a binary mask of a cornea of the eye; segmenting, based on the binary mask of the cornea of the eye, an anterior cornea of the eye on the OCT image; generating, based on the OCT image and the segmented anterior cornea, a binary mask for an epithelium layer of the eye; segmenting, based on the binary mask for the epithelium layer of the eye, a Bowman's layer in the cornea of the eye on the OCT image; and causing the segmented anterior cornea and the segmented Bowman's layer data to be used for generation of an epithelium map.

15 Claims, 7 Drawing Sheets

(51) Int. Cl.
    *A61B 3/107*     (2006.01)
    *G06T 7/136*     (2017.01)
    *G06T 7/149*     (2017.01)
    *G06T 7/70*     (2017.01)

(52) U.S. Cl.
    CPC ............... *G06T 7/149* (2017.01); *G06T 7/70* (2017.01); *G06T 2207/10101* (2013.01); *G06T 2207/20116* (2013.01); *G06T 2207/30041* (2013.01)

(58) Field of Classification Search
    CPC . G06T 2207/10101; G06T 2207/20116; G06T 2207/30041; G06T 7/0012; A61B 3/102; A61B 3/107
    See application file for complete search history.

(56) References Cited

U.S. PATENT DOCUMENTS

| | | | | |
|---|---|---|---|---|
| 10,748,287 | B2* | 8/2020 | Dhaini | G06T 7/0014 |
| 2013/0208240 | A1* | 8/2013 | Sharma | G06T 7/11 356/479 |
| 2019/0209006 | A1* | 7/2019 | Abou Shousha | A61B 3/103 |
| 2021/0177253 | A1* | 6/2021 | Bagherinia | A61B 3/0025 |
| 2022/0245769 | A1* | 8/2022 | Galeotti | G06T 7/12 |

OTHER PUBLICATIONS

Li et al., "Segmentation of 830- and 1310-nm LASIK corneal optical coherence tomography images," 2002, SPIE, Medical Imaging 2002: Image Processing, vol. 4684, pp. 167-178, https://doi.org/10.1117/12.467123 (Year: 2002).*

Wang et al., "BG-CNN: A Boundary Guided Convolutional Neural Network for Corneal Layer Segmentation from Optical Coherence Tomography," Aug. 2020, Association for Computing Machinery, https://doi.org/10.1145/3417519.3417560 (Year: 2020).*

Ouyang et al., "Accurate Tissue Interface Segmentation via Adversarial Pre-Segmentation of Anterior Segment OCT Images," 2019, arXiv, 2019 Optical Society of America (Year: 2019).*

Helwe et al., "A Deep Learning Approach to Detect the Demarcation Line in OCT Images," J. (eds) Medical Image Understanding and Analysis. MIUA 2020. Communications in Computer and Information Science, vol. 1248. Springer, Cham. https://doi.org/10.1007/978-3 (Year: 2020).*

Dhommati et al., "Automated 2D-3D quantitative analysis of corneal graft detachment post DSAEK based on AS-OCT images," 2018, Computer Methods and Programs in Biomedicine, vol. 167, pp. 1-12, https://doi.org/10.1016/j.cmpb.2018.10.003 (Year: 2018).*

George et al., "Two stage contour evolution for automatic segmentation of choroid and cornea in OCT images," 2019, Biocybernetics and Biomedical Engineering, Jul.-Sep. 2019, vol. 39, issue 3, pp. 686-696 (Year: 2019).*

Elsawy et al., "Deep Learning for the Segmentation and Classification of Optical Coherence Tomography Images of the Eye," Nov. 5, 2020, University of Miami, CoE—Electrical & Computer Engineering, Dissertation for Doctor of Philosophy (PhD) (Year: 2020).*

Shen et al., "Extended scan depth optical coherence tomography for evaluating ocular surface shape," 2011, Journal of Biomedical Optics, vol. 16, No. 5, https://doi.org/10.1117/1.3578461 (Year: 2011).*

Li, Yan, "Image Processing and Clinical Applications of Anterior Segment Optical Coherence," 2008, Doctor of Philosophy, Case Western Reserve University, Biomedical Engineering [online]. Retrieved from Internet <URL: http://rave.ohiolink.edu/etdc/view?acc_num=case1212436115> (Year: 2008).*

Elsawy Amr et al.: "Pathological-Corneas Layer Segmentation and Thickness Measurement in OCT Images", Translational Vision Science & Technology, vol. 9, No. 11, Oct. 21, 2020.

Hossein Rabbani et al.: "Obtaining Thickness Maps of Corneal Layers Using the Optimal Algorithm for Intracorneal Layer Segmentation", International Journal of Biomedical Imaging, vol. 2016, 2016, pp. 1-11, Article ID 1420230.

Tejas Sudharshan Mathai et al.: "Learning to Segment Corneal Tissue Interfaces in OCT Images", arxiv.org, Cornell University Library, 201 Oline Library Cornell University Ithaca, NY 14853, Oct. 15, 2018.

Williams Dominic et al.: "Automatic segmentation of anterior segment optical coherence tomography images", Journal of Biomedical Optics, vol. 18, No. 5, May 2013, 056003.

Dos Santos, V. A., Schmetter, L., Stegmann, H., Pfister, M., Messner, A., Schmidinger, G., Garhofer, G., & Werkmeister, R. M. (2019). CorneaNet: fast segmentation of cornea OCT scans of healthy andkeratoconic eyes using deep learning. Biomedical optics express, 10 (2), 622-641, https://doi.org/10.1364/BOE.10.000622.

Jahromi M. K., Kafleh R., Rabbani H., Dehnavi A. M., Peyman A., Hajizadah F., Ommani M., "An Automatic Algorithm for Segmentation of the Boundaries of Corneal Layers in Optical Coherence Tomography Images using Gaussian Mixture Model," J. Med. Signals Sensors 4, 171-180 (2014).

Yazdanpanah A, Hamareh G, Smithh B, Sarunic M., Intra-retinal layer segmentation in optical coherence tomography using an active contour approach. Med Image Comput Comput Assist Interv. 2009;12(Pt 2):649-656. doi:10.1007/978-3-642-04271-3_79.

\* cited by examiner

CORNEAL EPITHELIUM SEGMENTATION IN OPTICAL COHERENCE TOMOGRAPHY IMAGES

CROSS-REFERENCE TO RELATED APPLICATIONS

This application claims priority to and benefit of U.S. Provisional Patent Application No. 63/112,833, filed Nov. 12, 2020, the entire contents of which are incorporated by reference herein in its entirety.

BACKGROUND

Embodiments of the present disclosure generally relate to methods and apparatus for ophthalmic image segmentation, and more particularly, to methods and apparatus for segmenting corneal epithelium of an eye in optical coherence tomography (OCT) images generated based on scan data from an ophthalmic scanning device.

Ophthalmic diagnosis systems, such as OCT devices, are configured to generate OCT images of a patient's eye. Such images can be valuable diagnostic tools for clinicians, such as physicians and other users of the OCT devices. For example, certain information related to one or more structures of the eye can be extracted based on the OCT images. Extracting such information from the OCT images generally may require segmentation of one or more areas, structures, and/or tissues of the eye from the OCT image.

However, segmenting areas, structures, and/or tissues of the eye from one or more OCT images poses various challenges due to certain inherent characteristics of OCT images. For example, OCT images may suffer from speckle noise and/or other image interferences that can increase the difficulty for computing systems in identifying and segmenting the different structures or tissues of the scanned eye.

Furthermore, sufficient relevant image data (e.g., sample and/or reference OCT images of scanned eyes) for one or more structures and/or tissues of the eye may not be available to develop and train a model (e.g., machine learning model) that can satisfy the high accuracy standards of medical diagnostics when identifying and segmenting one or more structures and/or tissues of a scanned eye. Such lack of relevant image data prevents existing image segmentation systems and techniques from satisfying the accuracy and performance standards and requirements to deliver real-time and/or near real-time diagnostic information to clinicians.

SUMMARY

The present disclosure generally relates to methods and apparatus for segmenting corneal epithelium of an eye in an OCT image for providing diagnostic information.

In certain embodiments, a method of segmenting an optical coherence tomography (OCT) image generally includes receiving an OCT image of an eye. The method further includes generating, based on the OCT image, a binarized image of the eye. The method also includes generating, based on the binarized image of the eye and the OCT image, a binary mask of a cornea of the eye. The method further includes segmenting, based on the binary mask of the cornea of the eye, an anterior cornea of the eye on the OCT image. The method further includes generating, based on the OCT image and the segmented anterior cornea of the eye, a binary mask for an epithelium layer of the eye. The method also includes segmenting, based on the binary mask for the epithelium layer of the eye, a Bowman's layer in the cornea of the eye on the OCT image. The method further includes causing the segmented anterior cornea and the segmented Bowman's layer data to be used for generation of an epithelium map.

In certain embodiments, an optical coherence tomography (OCT) system generally includes a memory comprising computer-executable instructions. The OCT system further includes a processor configured to execute the computer-executable instructions and cause the OCT system to generate an OCT image of an eye. The processor is further configured to cause the OCT system to generate, based on the OCT image, a binarized image of the eye. The processor is further configured to cause the OCT system to generate, based on the binarized image of the eye and the OCT image, a binary mask of a cornea of the eye. The processor is further configured to cause the OCT system to segment, based on the binary mask of the cornea of the eye, an anterior cornea of the eye on the OCT image. The processor is further configured to cause the OCT system to generate based on the OCT image and the segmented anterior cornea of the eye, a binary mask for an epithelium layer of the eye. The processor is further configured to cause the OCT system to segment, based on the binary mask for the epithelium layer of the eye, a Bowman's layer in the cornea of the eye on the OCT image. The processor is further configured to cause the segmented anterior cornea and the segmented Bowman's layer data to be used for generation of an epithelium map.

In another embodiment, an imaging system, comprises: a memory comprising computer-executable instructions; a processor configured to execute the computer-executable instructions and cause the imaging system to: generate an optical coherence tomography (OCT) image of an eye; generate, based on the OCT image, a binarized image of the eye; generate, based on the binarized image of the eye and the OCT image, a binary mask of a cornea of the eye; segment, based on the binary mask of the cornea of the eye, an anterior cornea of the eye on the OCT image; generate, based on the OCT image and the segmented anterior cornea of the eye, a binary mask for an epithelium layer of the eye; segment, based on the binary mask for the epithelium layer of the eye, a Bowman's layer in the cornea of the eye on the OCT image; and cause the segmented anterior cornea and the segmented Bowman's layer data to be used for generation of an epithelium map. in this embodiment, the segmented Bowman's layer is the upper boundary of the binary mask for the epithelium layer.

Aspects of the present disclosure provide means for, apparatus, processors, and computer-readable mediums for performing the methods described herein.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
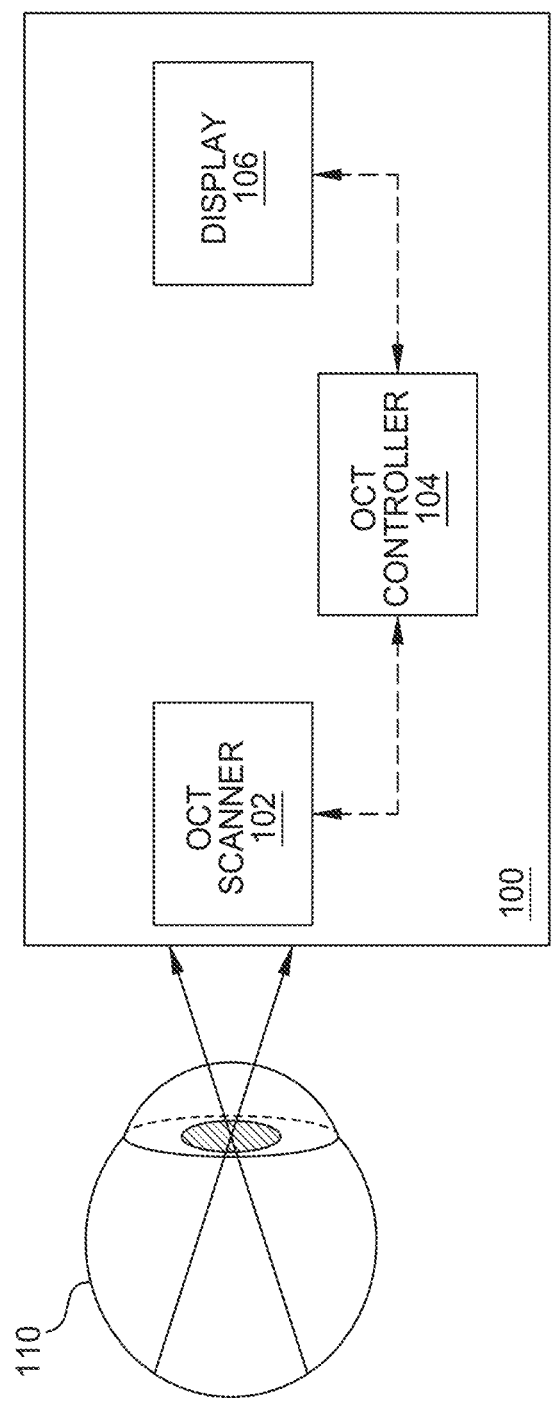
FIG. 1 illustrates a block diagram of selected components of an example imaging system, in accordance with certain embodiments of the present disclosure.

The present disclosure generally relates to methods and apparatus for segmenting corneal epithelium of an eye in an OCT image for providing diagnostic information.

OCT images of scanned eyes can be valuable diagnostic tools for clinicians as they can provide valuable diagnostic information about the scanned eye. Recent developments in OCT imaging has allowed imaging of certain structures or tissues of the eye that were not previously visible or captured in an OCT image. Examples of such recent developments in OCT imaging are the advancements in corneal OCT, which have made the corneal epithelium layer visible in the OCT image. The visibility of such structures of the eye in the OCT images can provide useful diagnostic information for the clinicians. For example, the visibility of the corneal epithelium layer of the eye can be used to produce an epithelium map, which can be used by clinicians and/or other diagnostic systems to determine whether patients undergoing eye surgeries (e.g., refractive eye surgeries) are at risk of certain postoperative issues (e.g., postoperative ectasia).

To extract the relevant diagnostic information of the eye, one or more portions or structures of the eye, which are of diagnostic interest to the clinician, may have to be segmented from the OCT images. However, OCT images can suffer from certain interferences, such as speckle noise and the like. Presence of such interferences can degrade the accuracy and performance of systems and techniques used for image segmentation. For example, presence of such interferences can cause discontinuity or blurriness in or near the boundaries of different structures or tissues of the eye. Existing image segmentation systems and techniques can have difficulty with accurately segmenting the structures or tissues of the eye in an OCT image due to the discontinuities or blurriness in or near the boundaries of the structures or tissues of the eye in the OCT images. Furthermore, certain structures and tissues of the eye, due to their size, when captured in the OCT images have low contrast and may be too thin for accurately segmenting the structures and tissues by the existing image segmentation systems and techniques. For example, the corneal epithelium layer of the eye may have thin dimensions, which when captured in the OCT image, can have low contrast and thin boundary layers that can cause errors when segmenting the corneal epithelium layer in the OCT image.

Additionally, when segmenting a structure or tissue of the eye in an image, generally features relevant to that structure must be extracted and segmentation of the structure is based on the extracted features. The features relevant to the structures can be identified and extracted using image segmentation models trained on OCT image data comprising the structures and/or tissues of the eye. However, for certain structures and/or tissues of the eye, identifying such deterministic features can be difficult when sufficient image data comprising such structures and/or tissues are not available. For example, sufficient amount of annotated OCT image data comprising corneal epithelium layer does not exist to train an image segmentation model that can accurately identify and segment the corneal epithelium in OCT images.

Therefore, to accurately segment the corneal epithelium layer of an eye, a large set of annotated OCT image data comprising corneal epithelium layers of eyes will be needed to develop image segmentation models that can accurately segment a corneal epithelium layer of a scanned eye. Additionally, the amount of such annotated OCT image data must be sufficiently large enough to ensure that these image segmentation models are trained to satisfy the accuracy and performance requirements to be used for medical diagnosis. However, generating a sufficiently large set of annotated OCT image data comprising corneal epithelium layers to develop and/or train an image segmentation model can consume significant compute resources of an image segmentation system and significant time resources such that it can be impractical in a real-world application to successfully train an image segmentation model to accurately segment OCT images for the desired structure and/or tissue of the scanned eye.

Accordingly, some implementations of the present disclosure provide various apparatuses, methods, and systems for segmenting a corneal epithelium layer of the eye in an OCT image, such as a corneal OCT image. As described herein, a corneal OCT image is a specific form of OCT image that presents the cornea and its sub layers of a scanned eye. In particular, the apparatuses, methods, and systems, as described herein, automatically segment the corneal epithelium layer from a corneal OCT image. Moreover, the apparatuses, methods, and systems described herein accurately segment a corneal epithelium layer in the corneal OCT image without extensive training of image segmentation models on a large set of annotated corneal OCT image data or OCT image data comprising data related to the corneal epithelium layer. Therefore, the techniques described herein improve the accuracy of image segmentation systems while significantly reducing the amount of training data, compute resources, and time resources needed to accurately segment corneal epithelium layer in a corneal OCT image.

FIG. 1 illustrates a block diagram of selected components of an example imaging system 100. The imaging system 100 includes an optical coherence tomography (OCT) scanner 102, an OCT controller 104, and a display 106.

The OCT scanner 102 may include a number of OCT components and/or instruments (not shown separately). The OCT components and/or instruments may be of various types, and the OCT scanner 102 may be configured differently based on the types of the OCT components and/or instruments. In some implementations, the OCT scanner 102 may be configured as a time domain OCT (TD-OCT). In some implementations, the OCT scanner 102 may be configured as a frequency domain OCT (FD-OCT). In some implementations, the OCT scanner 102 may be configured as a swept-source OCT (SS-OCT).

The OCT scanner 102 performs OCT scanning of an eye 110 of a patient. The OCT scanner 102 may perform the OCT scanning by controlling output of one or more sample beams (not shown) onto the eye 110, and receiving one or more measurement beams (not shown) reflected back from the eye 110. The one or more measurement beams may be reflected back from the eye 110 in response to the photons of the sample beam interacting with the tissue in the eye 110. The OCT scanner 102 may be configured to move the sample beam to a certain location of the eye in response to receiving a command and/or location information from the OCT controller 104.

The OCT scanner 102 may be configured to scan the eye 110 at various depths of the eye 110. For example, the OCT scanner 102 may be configured to scan the entire depth of the eye 110 for a full eye scan of the eye 110. Similarly, the OCT scanner 102 may be configured to scan any portion of the eye 110, such as the retina of the eye 110. In some implementations, the OCT scanner 102 may scan different depths of the eye 110 at different resolutions. For example, the OCT scanner 102 may scan the entire depth of the eye 110 at a lower resolution, and may scan a portion of the eye 110, such as the retina, cornea and its sub layers, and the like, of the eye 110, at a higher resolution.

The OCT scanner 102 may be configured to generate scan data based on the one or more measurement beams reflected back from the eye. The scan data may represent a depth profile of the scanned tissue. In some implementations, the scan data generated by the OCT scanner 102 may include two-dimensional (2D) scan data of a line scan (B-scan). In some implementations, the scan data generated by the OCT scanner 102 may include three-dimensional (3D) scan data of an area scan (C-scan, en face). The OCT scanner 102 may be configured to transmit the generated scan data to the OCT controller 104. In some implementations, the OCT scanner 102 may be configured to transmit the generated scan data in real-time or near real-time. In some implementations, the OCT scanner 102 may be configured to transmit the generated scan data after the entire scanning operation is completed by the OCT scanner 102.

The OCT scanner 102 may be configured to initiate scanning of the eye 110 in response to receiving a command and/or instruction from the OCT controller 104. The OCT controller 104 may be configured to transmit a scan initiation command to the OCT scanner 102 in response to receiving an indication from a user, such as a surgeon, clinician, medical personnel, and the like, to initiate scanning of the eye. In some implementations, the indication from the user may provide information related to depth and/or location of the eye for scanning, and the OCT controller 104 may be configured to provide the received eye depth and/or location related information to the OCT scanner 102. For example, an indication received by the OCT controller 104 may indicate a full eye OCT scan, and the OCT controller 104 may transmit an instruction to the OCT scanner 102 that indicates a full eye OCT scan. Similarly, an indication received by the OCT controller 104 may indicate an OCT scan of the retina of the eye, and the OCT controller 104 may transmit an instruction to the OCT scanner 102 that indicates an OCT scan of the retina of the eye. Similarly, an indication received by the OCT controller 104 may indicate an OCT scan of the cornea and/or its sub-layers of the eye, and the OCT controller 104 may transmit an instruction to the OCT scanner 102 that indicates an OCT scan of the cornea and/or its sub-layers of the eye 110.

The OCT controller 104 may be configured to receive the indication to initiate scanning of the eye via a user interface (e.g., a graphical user interface (GUI)) and/or an input device (not shown). Input devices may be communicatively coupled to and/or incorporated with the imaging system 100. Examples of input devices include, but are not limited to, a key pad, a keyboard, a touch screen device configured to receive touch inputs, and the like.

The OCT controller 104 may be communicatively coupled to the OCT scanner 102 via one or more electrical and/or communication interfaces. In some implementations, the one or more electrical and/or communication interfaces may be configured to transmit data (e.g., scan data generated by the OCT scanner 102) from the OCT scanner 102 at a high transmission rate such that the OCT controller 104 may receive the data in real-time or near real-time from the OCT scanner 102.

The OCT controller 104 may be configured to generate one or more OCT images based on the received generated scan data from the OCT scanner 102. For example, the OCT controller 104 may be configured to generate a 2D image or a B-scan image based on the generated 2D scan data of a line scan. Similarly, the OCT controller 104 may be configured to generate a 3D image or a C-scan based on the generated 3D scan data of an area scan. The OCT images generated by the OCT controller 104 comprise the structures, tissues, and/or portions of the eye that were scanned by the OCT scanner 102. For example, if the OCT scanner 102 scanned the cornea and/or its sub-layers of the eye, then the generated scan data from the OCT scanner 102 may include data related to the cornea and/or the sub-layers, and the OCT image generated by the OCT controller 104 includes the cornea and/or its sub-layers. In some implementations, the OCT images generated by the OCT controller 104 may have a horizontal display resolution of approximately 4,096 pixels, less than 4096 pixels, or more than 4096 pixels (collectively referred to herein as 4K OCT images). The OCT controller 104 may be configured to perform image generation and/or image processing in real-time and/or near real-time.

The OCT controller 104 may be configured with one or more detection algorithms configured to detect the cornea of the eye 110 and/or the sub-layers of the cornea of the eye 110 and/or any portions of the cornea and/or its sub-layers. Examples of one or more sub-layers of the cornea of the eye 110 include, but are not limited to, the anterior cornea, the Bowman's layer, corneal epithelium layer, and the like. The OCT controller 104 may be configured with one or more auto-segmentation algorithms to auto-segment cornea and/or one or more sub-layers of the cornea, such as the anterior cornea, Bowman's layer, corneal epithelium layer, and the like, in an OCT image. Additional details of the auto-segmentation algorithms of the OCT controller 104 are described herein with respect to FIGS. 3, 4A, 4B, and 5.

In some implementations, the OCT controller 104 may be configured with one or more other tissue detection and/or auto-segmentation algorithms to detect and/or auto-segment those structures and/or tissue layers of the eye in the generated OCT images. Examples of such other structures and/or tissue layers of an eye that the OCT controller 104 may be configured to detect and/or auto-segment include, but are not limited to, fovea, retinal pigment epithelium (RPE), anterior surface of the cornea, retina, cornea, iris, pupil, anterior and posterior surface plus the position of the lens, and the like. The OCT controller 104 may be configured to apply one or more tissue detection and/or auto-segmentation algorithms on the received scan data from the OCT scanner 102 and/or the generated OCT images to detect and/or auto-segment one or more tissue layers of the scanned eye.

The OCT controller 104 may be configured to generate enhanced OCT images by generating and/or displaying one or more virtual markers on one or more OCT images (e.g., the generated OCT image, a received OCT image, and the like) to visually identify one or more detected and/or auto-segmented tissue layers of the eye. For example, the OCT controller 104 may be configured to detect and/or auto-segment the anterior cornea of the eye in an OCT image, and generate and/or display a virtual marker on the OCT image to visually identify a location of the anterior cornea and/or segment at least a portion of the anterior cornea. Similarly, the OCT controller 104 may be configured to detect and/or auto-segment the Bowman's layer of the cornea in an OCT image, and generate and/or display a virtual marker on the OCT image to visually identify and/or segment the Bowman's layer of the cornea and/or a location of the Bowman's layer of the cornea.

The OCT controller 104 may be configured to generate and/or display the virtual markers in various shapes and/or sizes. For example, the OCT controller 104 may be configured to generate and/or display virtual markers that are curved, such as curvilinear lines. The OCT controller 104 may be configured to generate enhanced OCT images by generating and/or displaying virtual markers on OCT images (e.g., the OCT images generated by the OCT controller 104).

The OCT controller 104 may be configured to cause OCT images and/or the enhanced OCT images to be displayed to a user by providing the images to the display 106. The OCT controller 104 may be communicatively coupled and/or electrically connected to the display 106. The display 106 may be configured in compliance with one or more display standards and may be of any various types of displays, such as video graphics array (VGA), extended graphics array (XGA), digital visual interface (DVI), high-definition multimedia interface (HDMI), and the like.

The OCT controller 104 may be configured to cause the segmented anterior cornea and the segmented Bowman's layer data to be used for generation of an epithelium map. In some implementations, the OCT controller 104 may be configured to store the position data of the segmented anterior cornea and/or the segmented Bowman's layer in the OCT image in a data storage unit (not shown separately) communicatively coupled to the OCT controller 104. In some implementations, the OCT controller 104 may be configured to transmit the position data and/or the image data of the segmented anterior cornea and the segmented Bowman's layer to an epithelium map generation module (not shown). In some implementations, the epithelium map generation module may be located in a system remote to imaging system 100. For example, in some implementations, the epithelium map generation module may be located in a computing device that is communicatively coupled (e.g., a server computer) to the imaging system 100, and the OCT controller 104 may be configured to transmit the position and/or image data of the segmented anterior cornea and the segmented to Bowman's layer to the communicatively coupled server.

Figure 2:
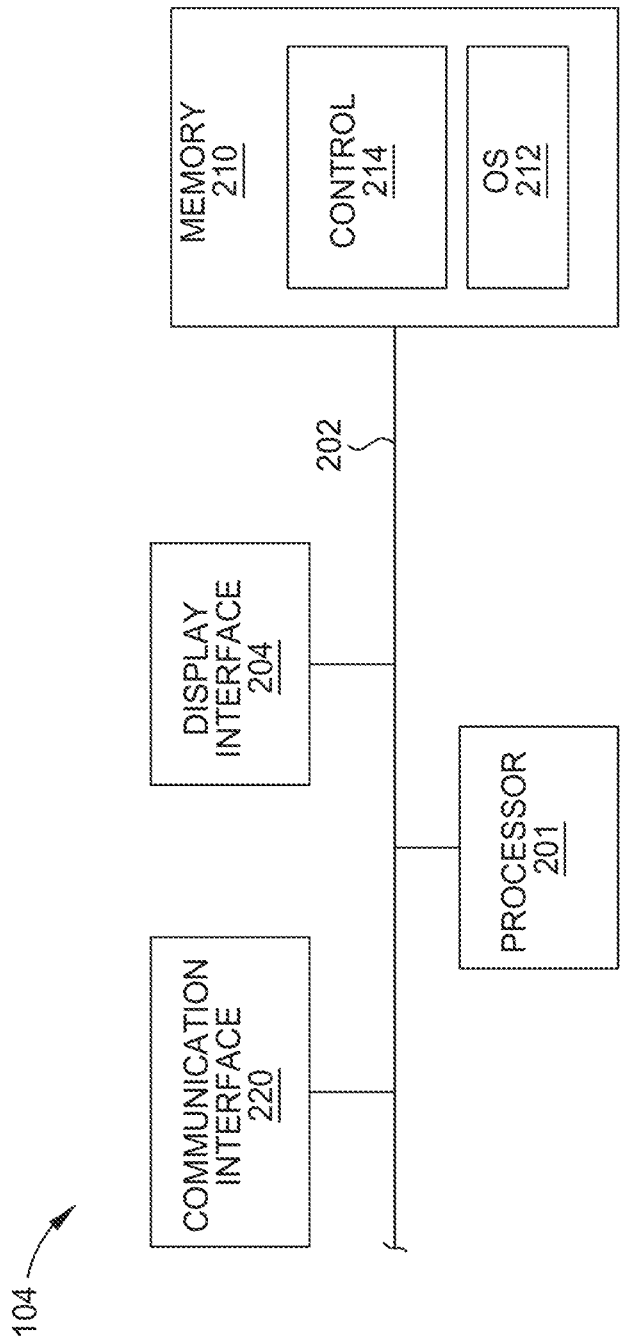
FIG. 2 illustrates a block diagram of selected components of an OCT controller, in accordance with certain embodiments of the present disclosure.

FIG. 2 illustrates a block diagram of selected components of an implementation of an OCT controller, such as the OCT controller 104 as described above in reference with FIG. 1. As shown in FIG. 2, OCT controller 104 includes processor 201, bus 202, display interface 204, memory 210, and communication interface 220.

The processor 201 is communicatively coupled to memory 210, display interface 204, and communication interface 220 via bus 202. The OCT controller 104 may be configured to interface with various external components (e.g., OCT scanner 102, display 106) of an imaging system (e.g., imaging system 100) via processor 201 and communication interface 220. In some implementations, communication interface 220 is configured to enable OCT controller 104 to connect to a network (not shown). In some implementations, the OCT controller 104 is connected to one or more displays, such as display 106, via display interface 204.

The memory 210 may include persistent, volatile, fixed, removable, magnetic, and/or semiconductor media. The memory 210 is configured to store one or more machine-readable commands, instructions, data, and/or the like. In some implementations, as shown in FIG. 2, the memory 210 includes one or more sets and/or sequences of instructions, such as an operating system 212, a scanning control application 214, and the like. Examples of operating system 212 may include, but are not limited to, UNIX or UNIX-like operating system, a Windows® family operating system, or another suitable operating system. The scanning control application 214 may be configured to perform OCT controller operations as described herein including, but not limited to, operations related to initiation of scanning of the eye, generation of OCT images, OCT image processing, generation and/or displaying of virtual markers on OCT images, generation of enhanced OCT images, and the like.

Figure 3:
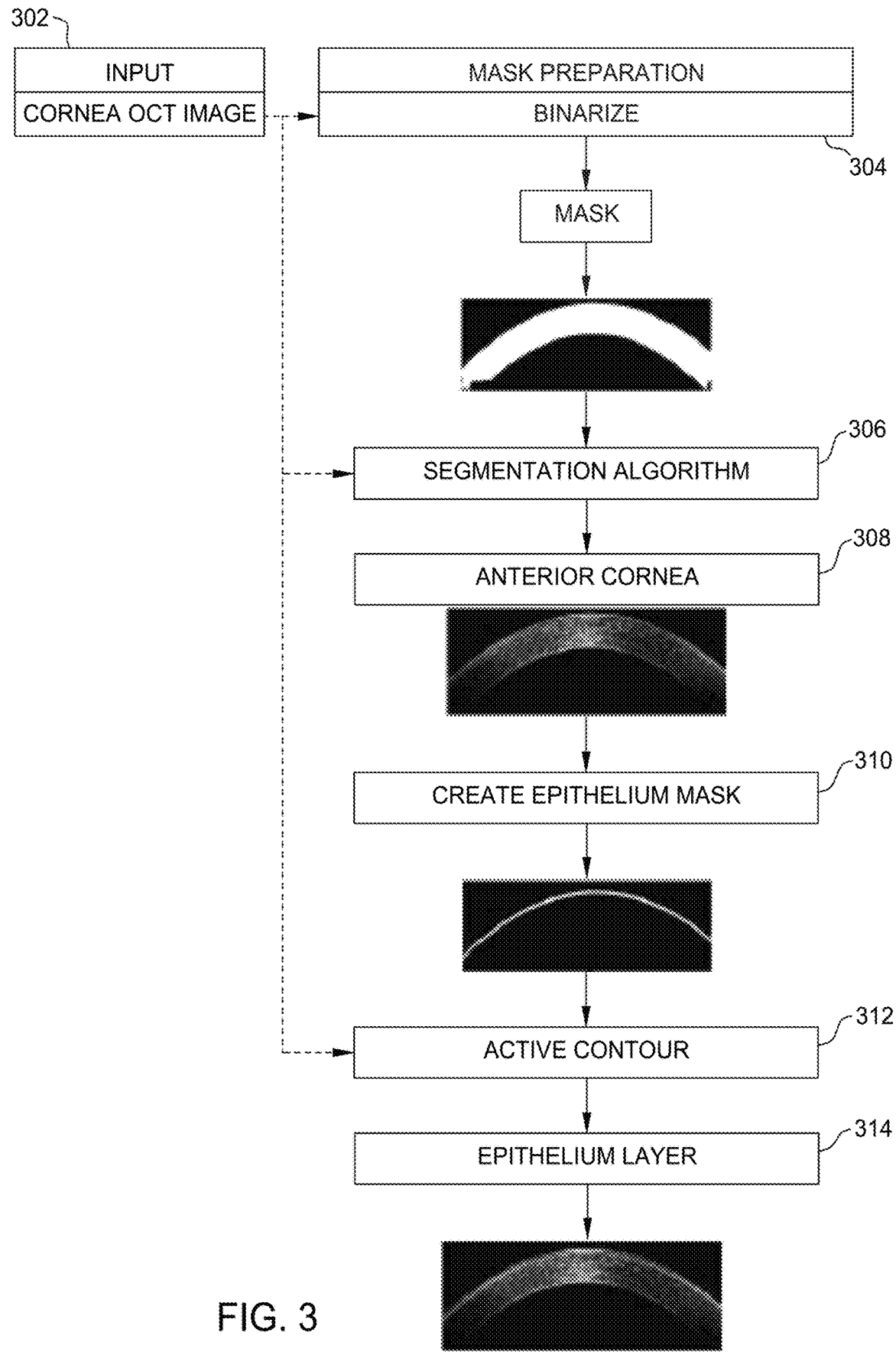
FIG. 3 illustrates an example flow chart for segmenting a corneal epithelium layer in an OCT image, in accordance with certain embodiments of the present disclosure.

FIG. 3 illustrates an example flow chart to segment a corneal epithelium layer in an OCT image, in accordance with an illustrative implementation of the present disclosure. The operations 300 may be performed, for example, by an OCT controller (e.g., the OCT controller 104 of imaging system 100). The operations 300 may be implemented as software components that are executed on one or more processors (e.g., processor 201).

The operations 300 may begin at operation 302, where an OCT image displaying a cornea (e.g., a cornea OCT image), corresponding to a scanned cornea of an eye, is generated and/or received by the OCT controller 104. As described above, the OCT controller 104 may be configured to generate the cornea OCT image based on the scan data received from the OCT scanner 102. In some implementations, the OCT controller 104 may be configured to receive the cornea OCT image from another component of the imaging system 100. For example, the imaging system 100 may comprise an image generator that is communicatively coupled to the OCT scanner 102, and the image generator may be configured to generate a cornea OCT image based on the scanned data of the OCT scanner 102. In some implementations, the image generator and/or the OCT controller 104 may be configured to generate a 4K cornea OCT image comprising the cornea based on the scanned data of the OCT scanner 102.

Figure 4B:
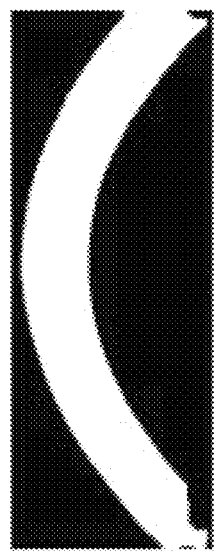
FIG. 4B illustrates an example binarized image of an OCT image of a cornea, in accordance with certain embodiments of the present disclosure.
Figure 4A:
FIG. 4A illustrates an example OCT image of a cornea, in accordance with certain embodiments of the present disclosure.

An example of a cornea OCT image generated by an image generator of the image system 100 or the OCT controller 104 is shown in FIG. 4A. The OCT image shown in FIG. 4A comprises a cornea of an eye. As shown in FIG. 4A, the OCT image includes speckle noise in certain portions of the OCT image. Returning to FIG. 3, at operation 304, the cornea OCT image is binarized to generate a mask for the cornea. The cornea OCT image is binarized to determine a location of the cornea and/or a portion of the cornea in the cornea OCT image. An example of a binarized cornea OCT image, representing an initial binary mask of the cornea, is shown in FIG. 4B. As shown in FIG. 4B, the portion of the OCT image displaying the cornea is displayed in the binarized OCT image in a lighter color in the foreground, and the portions of the OCT image not displaying the cornea (e.g., background portions of the image) are shown in a darker color in the background of the binarized image of FIG. 4B.

At operation 306, the initial mask shown in FIG. 4B is further adjusted and/or refined to generate a final mask for the cornea in the OCT image that accurately captures the shape and size of the cornea in the OCT image. In some implementations, the final mask for the cornea may be generated by iteratively adjusting the initial mask using one or more segmentation and/or extraction algorithms, such as the Chan-Vese active contour algorithm. In some implementations, the final mask of the cornea may be generated by contracting (e.g., shrink-inward) or expanding (e.g., grow-outward) the foreground portion of the initial mask of the cornea. For example, the OCT controller 104 may apply the Chan-Vese active contour algorithm iteratively to the initial mask generated at operation 304 until a terminal condition is satisfied. Through the iterative application of the Chan-Vese active contour algorithm, the OCT controller 104 may contract (e.g., shrink-inward) or expand (e.g., grow-outward) the foreground portion of the mask representative of the cornea area. Examples of a terminal condition include, but are not limited to, a predetermined number of iterations, a predetermined number of expansions and/or contractions of the cornea area, and the like.

Figure 4D:
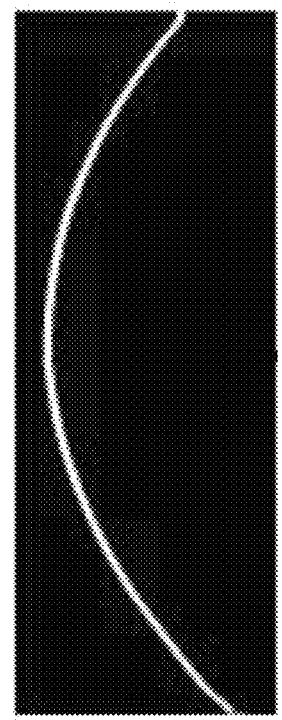
FIG. 4D illustrates an example initial mask for the corneal epithelium layer of a scanned eye, in accordance with certain embodiments of the present disclosure.
Figure 4C:
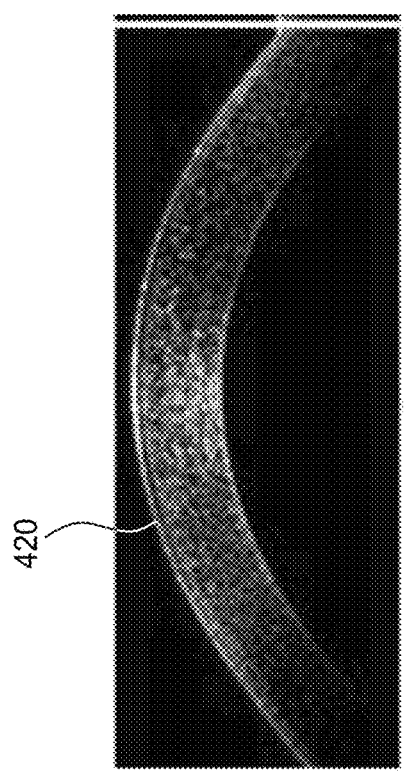
FIG. 4C illustrates an example enhanced OCT image of a cornea, in accordance with certain embodiments of the present disclosure.

The OCT controller 104 may be configured to identify the upper boundary of the final mask of the cornea as the upper boundary of the anterior cornea of the scanned eye. At operation 308, the OCT controller 104 applies the final mask of the cornea to the cornea OCT image to segment the portion of the cornea in the cornea OCT image that corresponds to the upper boundary of the final mask of the cornea, as anterior cornea. The OCT controller 104 may store position information of the detected and segmented anterior cornea in a storage unit communicatively coupled to the OCT controller 104. In some implementations, the OCT controller 104 may display virtual indicators on the OCT image corresponding to the segmented anterior cornea, as shown in FIG. 4C. In FIG. 4C, the virtual indicator 420 displays the segmented anterior cornea.

Returning to FIG. 3, at operation 310, the OCT controller 104 generates an initial mask for the corneal epithelium layer of the scanned eye. The OCT controller 104 may be configured to generate the initial mask for the corneal epithelium layer based on the position of the segmented anterior cornea and a determined position of the Bowman's layer. The OCT controller 104 may be configured to determine the position of the Bowman's layer based on a predetermined thickness of the corneal epithelium layer and/or a predetermined distance from the anterior cornea where the Bowman's layer is expected to be present. An example of an initial mask for the corneal epithelium layer of a scanned eye is shown in FIG. 4D.

At step 312, the OCT controller 104 generates the final mask for the corneal epithelium layer. The OCT controller 104 may be configured to generate the final mask for the corneal epithelium layer based on the cornea OCT image, the initial mask, and/or one or more segmentation and/or extraction algorithms, such as the Chan-Vese active contour algorithm. In some implementations, the OCT controller 104 may generate the final mask for the corneal epithelium layer by iteratively contracting and/or expanding the portions of the initial mask representing the corneal epithelium layer. In some implementations, similar to the manner in which the final mask of the cornea is generated, the OCT controller 104 may generate the final mask for the corneal epithelium layer by applying the Chan-Vese active contour algorithm to the initial mask for the corneal epithelium layer to iteratively contract and/or expand the portion of the mask representing the corneal epithelium layer. The OCT controller 104 may be configured to apply the Chan-Vese active contour algorithm until a terminal condition is satisfied.

At operation 314, the OCT controller 104 segments the Bowman's layer in the OCT image based on the final mask for the corneal epithelium layer. The OCT controller 104 may be configured to segment the upper boundary of the final mask as the Bowman's layer or a boundary of the Bowman's layer. In some implementations, the OCT controller 104 may be configured to segment the upper boundary of the final mask for the corneal epithelium layer as the bottom boundary of the Bowman's layer. The OCT controller 104 may be configured to display virtual indicator, such as virtual indicator 440, on the OCT image identifying the boundary of the Bowman's layer (e.g., bottom boundary of the Bowman's layer), as shown in FIG. 4E.

Figure 4F:
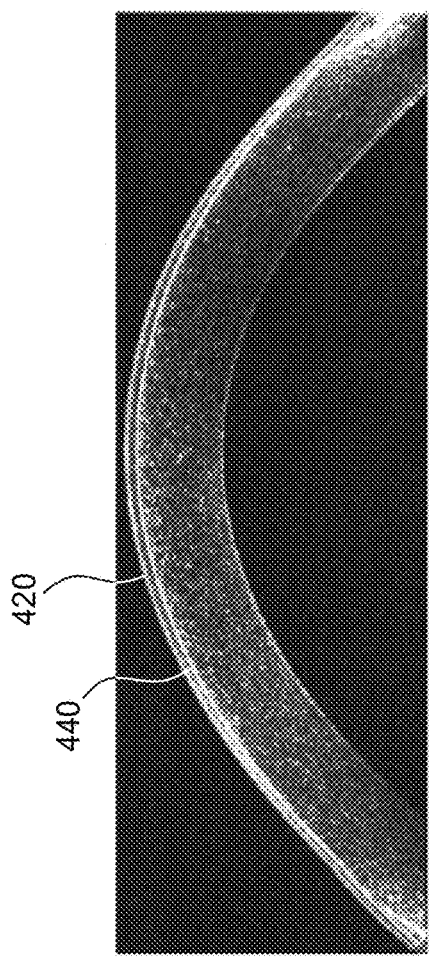
FIG. 4F illustrates an example enhanced OCT image of a cornea, in accordance with certain embodiments of the present disclosure.
Figure 4E:
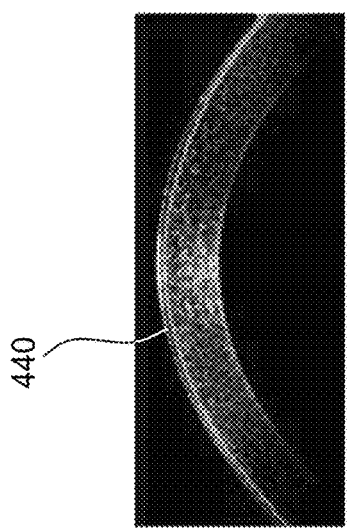
FIG. 4E illustrates an example enhanced OCT image of a cornea, in accordance with an illustrative implementation of the present disclosure.

The OCT controller 104 may display virtual indicators (e.g., 420 and 440) identifying the segmented anterior cornea and the segmented Bowman's layer on an OCT image, as shown in FIG. 4F. The OCT controller 104 may be configured to segment the portion of the cornea between the segmented anterior cornea and the segmented Bowman's layer as the corneal epithelium layer in the generated and/or received OCT image.

Therefore, the techniques described herein for binarizing OCT images of cornea and generating masks, to accurately identify and segment anterior cornea and the Bowman's layer, allow for accurate segmentation of the corneal epithelium layer without generating and training on large sets of image data comprising cornea and its sub-layers. Thus, the techniques described herein improve the accuracy of image segmentation systems while utilizing significantly fewer compute resources, data resources, and time resources.

Figure 5:
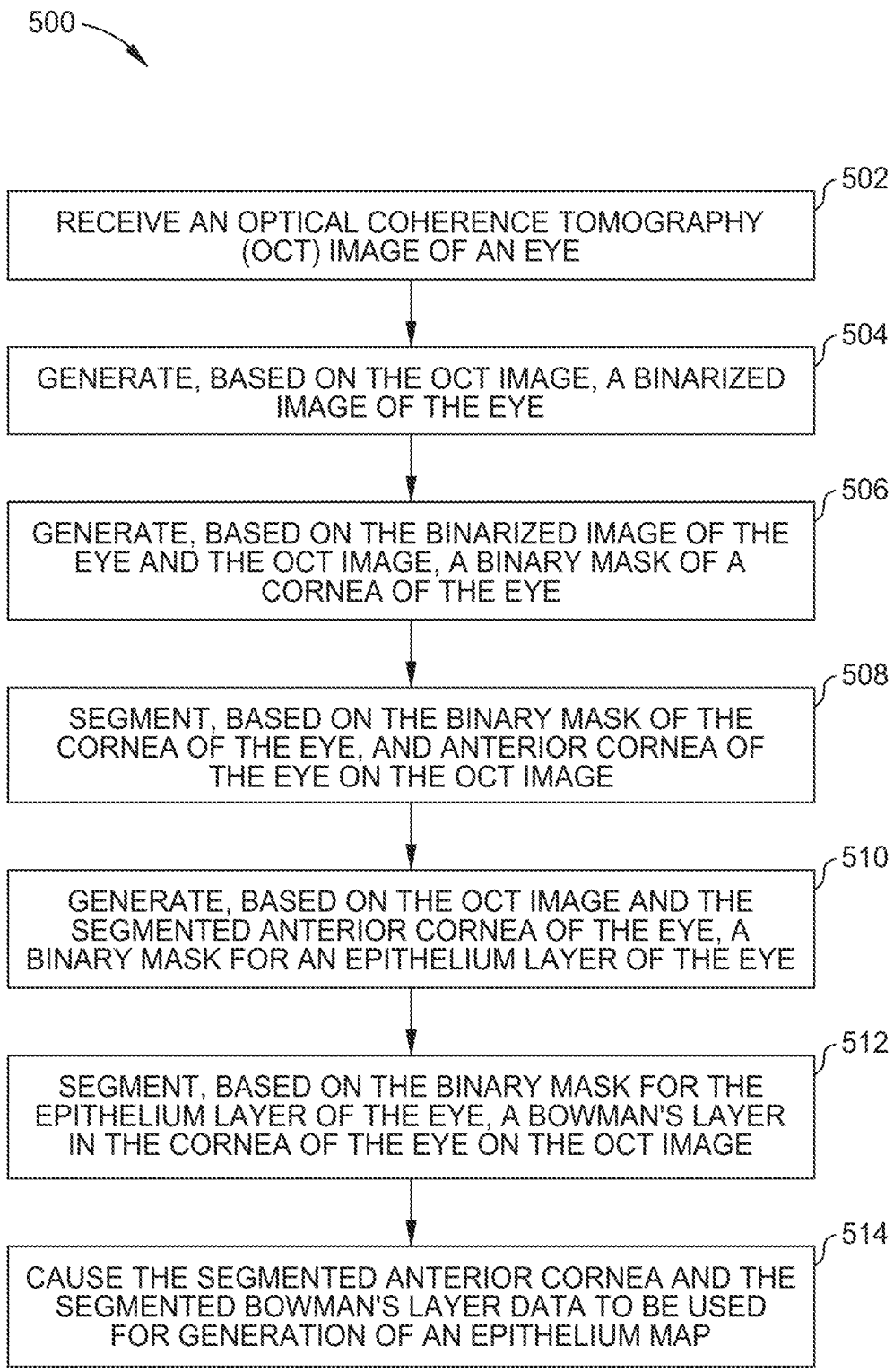
FIG. 5 illustrates a flow chart of an example method for segmenting corneal epithelium layer, in accordance with certain embodiments of the present disclosure.

FIG. 5 illustrates a flow chart of an example method for segmenting a corneal epithelium layer in ophthalmic images, in accordance with an illustrative implementation of the present disclosure. The operations 500 may be performed, for example, by an OCT controller (e.g., the OCT controller 104 of imaging system 100). The operations 500 may be implemented as software components that are executed and run on one or more processors (e.g., processor 201).

The operations 500 may begin at 502, where the OCT controller 104 receives an OCT image of an eye. As described above, in some implementations, the OCT controller 104 may generate the OCT image of an eye based on the scan data of the OCT scanner 102, and in some implementations, the OCT controller 104 may receive an the OCT image from an image generation component of an imaging system (e.g., imaging system 100). At 504, the OCT controller 104 generates, based on the OCT image, a binarized image of the eye. At 506, the OCT controller 104 generates, based on the binarized image of the eye and the OCT image, a binary mask of a cornea of the eye. At 508, the OCT controller 104 segments, based on the binary mask of the cornea of the eye, an anterior cornea of the eye on the OCT image. At 510, the OCT controller 104 generates, based on the OCT image and the segmented anterior cornea of the eye, a binary mask for an epithelium layer of the eye. At 512, the OCT controller 104 segments, based on the binary mask for the epithelium layer of the eye, a Bowman's layer in the cornea of the eye on the OCT image. At 514, the OCT controller 104 causes the segmented anterior cornea and the segmented Bowman's layer data to be used for generation of an epithelium map. In some implementations, as described above, the OCT controller 104 may transmit the position data in the OCT image and/or the image data of the segmented anterior cornea and the segmented Bowman's layer data to a computing module and/or device configured to generate an epithelium map in order to cause the generation of the epithelium map or the corneal epithelium map.

In some implementations, the OCT controller 104 identifies, based on the OCT image of the eye, a location of the cornea of the eye. In some implementations, the OCT controller 104 generates the binary mask of the cornea of the eye by iteratively adjusting a foreground portion of the binarized image of the eye. In some implementations, the OCT controller 104 iteratively adjusts the foreground portion of the binarized image of the eye by iteratively contracting or expanding the foreground portion of the binarized image of the eye.

In some implementations, the segmented anterior cornea is an upper boundary of the binary mask of the cornea of the eye. In some implementations, OCT controller 104 generates the binary mask for the epithelium layer of the eye by identifying, based on a position of the segmented anterior cornea on the OCT image of the eye and a predetermined epithelium thickness, a location of the epithelium layer. In some implementations, the location of the binary mask for the epithelium layer is based on the location of the epithelium layer. In some implementations, the segmented Bowman's layer is the upper boundary of the binary mask for the epithelium layer.

While the foregoing is directed to embodiments of the present disclosure, other and further embodiments of the disclosure may be devised without departing from the basic scope thereof, and the scope thereof is determined by the claims that follow.

What is claimed is:

1. A method for segmenting corneal epithelium layer in an optical coherence tomography (OCT) image of an eye, comprising:
    receiving the OCT image of the eye;
    generating, based on the OCT image, a binarized image of the eye;
    generating, based on the binarized image of the eye and the OCT image, a binary mask of a cornea of the eye;
    segmenting, based on the binary mask of the cornea of the eye, an anterior cornea of the eye on the OCT image;
    generating, with the OCT image and the segmented anterior cornea of the eye, a binary mask for an epithelium layer of the eye;
    segmenting, with the binary mask for the epithelium layer of the eye, a Bowman's layer in the cornea of the eye on the OCT image; and
    causing the segmented anterior cornea and the segmented Bowman's layer data to be used for generation of an epithelium map.

2. The method of claim 1 further comprising:
    identifying, based on the OCT image of the eye, a location of the cornea of the eye.

3. The method of claim 1, wherein generating the binary mask of the cornea of the eye further comprises:
    iteratively adjusting a foreground portion of the binarized image of the eye.

4. The method of claim 3, wherein iteratively adjusting the foreground portion of the binarized image of the eye further comprises:
    iteratively contracting or expanding the foreground portion of the binarized image of the eye.

5. The method of claim 1, wherein the segmented anterior cornea is an upper boundary of the binary mask of the cornea of the eye.

6. The method of claim 1, wherein generating the binary mask for the epithelium layer of the eye further comprises:
    identifying, based on a position of the segmented anterior cornea on the OCT image of the eye and a predetermined epithelium thickness, a location of the epithelium layer.

7. The method of claim 6, wherein a location of the binary mask for the epithelium layer is based on the location of the epithelium layer.

8. The method of claim 1, wherein the segmented Bowman's layer is an upper boundary of the binary mask for the epithelium layer.

9. An imaging system comprising:
    a memory comprising computer-executable instructions;
    a processor configured to execute the computer-executable instructions and cause the imaging system to:
        generate an optical coherence tomography (OCT) image of an eye;
        generate, based on the OCT image, a binarized image of the eye;
        generate, based on the binarized image of the eye and the OCT image, a binary mask of a cornea of the eye;
        segment, based on the binary mask of the cornea of the eye, an anterior cornea of the eye on the OCT image;
        generate with the OCT image and the segmented anterior cornea of the eye, a binary mask for an epithelium layer of the eye;
        segment with the binary mask for the epithelium layer of the eye, a Bowman's layer in the cornea of the eye on the OCT image; and
        cause the segmented anterior cornea and the segmented Bowman's layer data to be used for generation of an epithelium map.

10. The imaging system of claim 9, wherein the processor is further configured to cause the imaging system to:
    identifying, based on the OCT image of the eye, a location of the cornea of the eye.

11. The imaging system of claim 9, wherein the processor is further configured to generate the binary mask of the cornea of the eye by iteratively adjusting a foreground portion of the binarized image of the eye.

12. The imaging system of claim 11, wherein the processor is further configured to iteratively adjust the foreground portion of the binarized image of the eye by iteratively contracting or expanding the foreground portion of the binarized image of the eye.

13. The imaging system of claim 9, wherein the segmented anterior cornea is an upper boundary of the binary mask of the cornea of the eye.

14. The imaging system of claim 9, wherein the processor is further configured to generate the binary mask for the epithelium layer of the eye by identifying, based on a position of the segmented anterior cornea on the OCT image of the eye and a predetermined epithelium thickness, a location of the epithelium layer.

15. The imaging system of claim 14, wherein a location of the binary mask for the epithelium layer is based on the location of the epithelium layer.

\* \* \* \* \*